US 6,649,669 B2

(12) United States Patent
Dickens

(10) Patent No.: US 6,649,669 B2
(45) Date of Patent: Nov. 18, 2003

(54) SINGLE SOLUTION BONDING FORMULATION

(75) Inventor: Sabine Dickens, Montgomery Village, MD (US)

(73) Assignee: American Dental Association Health Foundation, Gaithersburg, MD (US)

(*) Notice: Subject to any disclaimer, the term of this patent is extended or adjusted under 35 U.S.C. 154(b) by 136 days.

(21) Appl. No.: 10/029,297

(22) Filed: Dec. 28, 2001

(65) Prior Publication Data

US 2003/0149129 A1 Aug. 7, 2003

(51) Int. Cl.[7] ............... C08F 2/50; C08F 2/48
(52) U.S. Cl. ................ 522/76; 522/14; 522/21; 522/33; 522/48; 522/71; 522/82; 522/79; 522/83; 522/84; 522/85; 522/86; 522/104; 522/107; 522/149; 522/150; 522/153; 522/154; 522/164; 522/178; 522/179; 522/908; 523/109; 523/115; 523/116; 523/118; 523/300
(58) Field of Search ................ 522/8, 14, 21, 522/33, 48, 71, 76, 77, 79, 82, 81, 83, 84, 85, 86, 104, 107, 149, 150, 153, 154, 164, 178, 179, 182, 908; 523/109, 116, 118, 115, 300

(56) References Cited

U.S. PATENT DOCUMENTS

| | | | | |
|---|---|---|---|---|
| 4,542,172 A | | 9/1985 | Jochum et al. | |
| 4,556,651 A | * | 12/1985 | Shibukawa et al. | 514/191 |
| 4,636,533 A | * | 1/1987 | Janda et al. | 522/14 |
| 4,640,936 A | * | 2/1987 | Janda et al. | 522/14 |
| 4,746,686 A | * | 5/1988 | Waller | 522/14 |
| 4,813,876 A | | 3/1989 | Wang | |
| 4,880,619 A | * | 11/1989 | Gaffar | 424/52 |
| 4,886,843 A | | 12/1989 | Walton | |
| 4,918,136 A | * | 4/1990 | Kawaguchi et al. | 524/751 |
| 5,053,212 A | * | 10/1991 | Constantz et al. | 423/305 |
| 5,141,560 A | * | 8/1992 | Combe et al. | 106/35 |
| 5,260,476 A | * | 11/1993 | Ohno et al. | 560/90 |
| 5,321,053 A | * | 6/1994 | Hino et al. | 522/26 |
| 5,338,773 A | * | 8/1994 | Lu et al. | 523/116 |
| 5,401,783 A | * | 3/1995 | Bowen | 523/116 |
| 5,508,342 A | | 4/1996 | Antonucci et al. | |
| 5,658,963 A | * | 8/1997 | Qian et al. | 522/14 |
| 5,749,733 A | * | 5/1998 | Qian et al. | 433/228.1 |
| 5,767,170 A | * | 6/1998 | Ibsen et al. | 522/81 |
| 5,883,153 A | * | 3/1999 | Roberts et al. | 523/116 |
| 6,001,897 A | | 12/1999 | Dickens | |
| 6,114,408 A | | 9/2000 | Dickens | |
| 6,147,137 A | * | 11/2000 | Jia | 523/118 |
| 6,187,838 B1 | | 2/2001 | Dickens | |
| 6,206,959 B1 | | 3/2001 | Dickens | |
| 6,210,759 B1 | | 4/2001 | Dickens | |
| 6,325,993 B1 | * | 12/2001 | Saito et al. | 424/49 |
| 6,398,859 B1 | * | 6/2002 | Dickens et al. | 106/35 |
| 6,521,264 B1 | * | 2/2003 | Lacout et al. | 424/602 |

* cited by examiner

*Primary Examiner*—Sanza L. McClendon
(74) *Attorney, Agent, or Firm*—Banner & Witcoff, Ltd.

(57) ABSTRACT

A single solution bonding formulation for dental applications comprising a plurality of at least one self-polymerizable polyvinyl acidic monomer or at least two different polymerizable polyvinyl acidic monomers, a calcium phosphate filler, at least one photoinitiator, optionally an accelerator, optionally a solvent, and optionally a fluoride additive is provided. Additionally, a method for treating enamel, dentin, and/or pulp with the same single solution bonding formulation is provided. The single solution bonding formulation provides for the release of calcium, phosphate and/or fluoride ions which are sufficient in situ to form hydroxyapatite and/or fluorapatite.

90 Claims, 4 Drawing Sheets

...... = threshold for hydroxyapatite (HA) formation.
---- = threshold for fluorapatite formation.
___ = threshold for DCPD formation.

SINGLE SOLUTION BONDING FORMULATION

FIELD OF THE INVENTION

The subject invention is directed to a single solution bonding formulation, a method for treating dentin or enamel with the same, and a method for making the single solution bonding formulation. More particularly, the subject invention is directed to a single solution bonding formulation which provides a physical barrier to bacteria, toxins and other caries producing agents while permitting fluoroapatite and/or hydroxyapatite to form under and/or around the physical barrier.

BACKGROUND OF THE INVENTION

Teeth are structured with an outer enamel layer, a middle dentin layer, and an inner pulp layer. The pulp contains the living tissue of the tooth, including vasculature and nerve endings. The dentin layer, which surrounds the pulp, contains mostly hydroxyapatite and collagen. Hydroxyapatite forms when calcium hydroxides react with phosphate in the proper amounts and under the right conditions. Hydroxyapatite has the formula $Ca_5(PO_4)_3OH$. Dentin may also contain fluorapatite. Fluorapatite forms when fluoride precipitates with calcium and phosphate in the proper amounts and under the right conditions. Fluorapatite has the formula $Ca_5(PO_4)_3F$. The enamel, which covers the dentin, is a very hard protective layer.

Bacteria present within the oral cavity convert sugar and starch into acid by-products. The acid by-products can dissolve the enamel layer of a tooth and create a hole in the enamel layer, called a cavity. The acid-by-products can then continue to react and dissolve the underlying dentin. Hydroxyapatite (e.g., in dentin) is particularly sensitive to acid dissolution. Ultimately, if left untreated, the pulp will be exposed to bacteria including their acid by-products and may eventually die as a result. Once substantial damage to the pulp has occurred, one may require a root canal to remove dead tissue. Also, other corrective steps (e.g., placement of post, cap, and crown) may be required to prevent further decay. It would be desirable to prevent tooth decay before reaching the point of requiring extensive root-canal work.

Thus, it would be more desirable to repair or reconstruct the damaged dentin or enamel before the pulp is infected or otherwise injured. Not only is it desirable to repair and/or reconstruct the damaged dentin or enamel, but it is also desirable to provide a physical barrier over the same dental structures to prevent further deterioration.

Treatment of damaged dental structures (e.g., dentin, enamel, etc.) typically consists of applying a bonding agent to a cavity to permanently adhere a restorative filling material, e.g. composite resin, to the tooth structure to provide a physical barrier against further damage by bacteria and their acid by-products. Exemplary bonding formulations are disclosed in U.S. Pat. Nos. 4,918,136; 5,767,170; 6,114,408; 6,206,959; and 6,210,759. Typical bonding agents used to treat a damaged tooth do not, however, promote repair of the underlying dental structures in situ.

Thus, there is great need for a formulation that has adhesive properties and acts as a physical barrier and yet promotes the in situ restoration and/or repair of the underlying dental structures (e.g., enamel and/or dentin) by inducing the precipitation of minerals such as hydroxyapatite and/or fluorapatite. It is desirable to provide the above-noted formulation in a single-solution (ie., avoid two-or-more multipart-formulations) type formulation for convenience, and ease of use.

BRIEF SUMMARY OF THE INVENTION

It is an object of this invention to provide a single solution bonding formulation for dental applications for bonding to dentin and/or enamel to provide a physical barrier against further deterioration while providing release of calcium, phosphate and/or fluoride sufficient to deposit fluorapatite and/or hydroxyapatite at the site of tissue, dentin or enamel damage.

It is another object of this invention to provide a method for preparing a single solution bonding formulation for bonding to dentin and/or enamel while providing release of calcium, phosphate and/or fluoride sufficient to incorporate fluorapatite and/or hydroxyapatite to strengthen, impart greater resistance to decay, and repair or restore missing or decayed dental structures.

It is still another object of this invention to provide a method for treating dentin, enamel, or pulp with the above noted single solution bonding formulation(s).

These and other objects of the invention are provided by one or more embodiments described below. In one embodiment, a single solution bonding formulation for dental applications is provided. The formulation comprises:

(a) a plurality of a self-polymerizable polyvinyl acidic monomer or a plurality of at least two different polymerizable polyvinyl acidic monomers,
(b) a calcium phosphate filler,
(c) at least one polymerization photoinitiator,
(d) optionally, an accelerator,
(e) optionally, a solvent, and
(f) optionally, a fluoride additive.

The monomers noted as (a) above should be provided in an amount sufficient to form a physical barrier over the dental structure, and mediate bonding between the tooth structure and an overlying restorative material, preferably with a shear bond strength of at least about 28 MPa.

According to another embodiment of the invention, a method for preparing the above-noted single solution bonding formulation is provided. The method comprises the step of:

mixing together:
(a) a plurality of a self-polymerizable polyvinyl acidic monomer or a plurality of at least two different polymerizable polyvinyl acidic monomers,
(b) a calcium phosphate filler,
(c) at least one polymerization photoinitiator,
(d) optionally, an accelerator,
(e) optionally, a solvent, and
(f) optionally, a fluoride additive.

According to still another embodiment of the invention, a method for treating enamel, dentin, or pulp, is provided. The method comprises the steps of:

(a) applying to the enamel, dentin, or exposed pulp the above-noted single solution bonding formulation; and
(b) then exposing the applied single solution bonding formulation to light sufficient to polymerize the single solution bonding formulation.

According to another embodiment of the invention, another method to treat enamel, dentin, or pulp is provided. Such a method further comprises conditioning the enamel, dentin, or pulp before applying the above noted single solution polymerization formulation as noted in step (a).

DETAILED DESCRIPTION OF THE INVENTION

Figure 1:
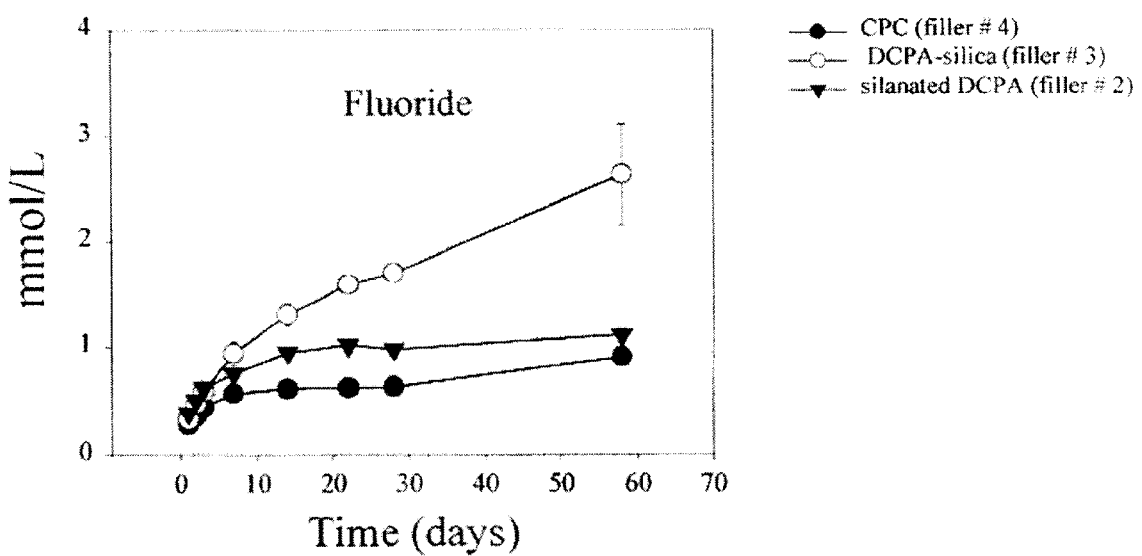
FIG. 1 is a plot of fluoride ion release (mmol/L) versus time wherein the fluoride ion release is from a single solution bonding formulation. The amount of fluoride released was measured with a fluoride ion selective electrode (Orion, Cambridge, Mass.). Fluoride standard solutions ranging from $1 \times 10^{-6}$ M to $1 \times 10^{-4}$ M were used to form a calibration curve, which was used to determine the fluoride concentration.

The term "sound enamel or dentin" means enamel and/or dentin of sufficient thickness, hardness, and/or structure substantially equivalent to that of a fully mineralized healthy tooth.

The term "polymerizable monomer" includes providing the subject "monomer" in a quantity sufficient for use in a single solution bonding formulation of the present invention for dental applications such as restorations of dental structures afflicted with caries in the enamel and/or dentin, repair of same, or cosmetic applications to same. The polymerizable monomer is provided in an amount sufficient to yield a shear bond strength of at least about 28 MPa when bonded to sound dentin and/or enamel.

The term "poly-vinyl" means at least two vinyl moieties.

The term "treating" includes, but is not limited to, restoration, repair, prophylaxis, and/or improvement of the dental structure. "Improvement" includes, but is not limited to, forming a well-adhered physical barrier to prevent further tooth decay, permitting formation of fluorapatite and/or hydroxyapatite underneath and/or around the formed physical barrier.

The term "microfine silica" means $SiO_2$ having an average particle diameter of about 0.04 μm.

The term "plurality" means being provided in a quantity sufficient to bond to enamel or dentin upon polymerization to provide a shear bond strength of at least about 28 MPa when bonded to sound enamel or dentin.

The term "nanofiller" means inert particles with average diameters in the nanometer range (i.e., from about 0.01 nm to about 1 nm).

The term "diffusion rate" refers to diffusion into saliva like solution (see Example 5) providing evidence for diffusion into the underlying and/or surrounding enamel, dentin or pulp of the components or ions (e.g., calcium phosphate and/or fluoride sufficient to form fluorapatite and/or hydroxyapatite) of the single solution bonding formulation after the formulation has been bonded to the afflicted enamel and/or dentin. "Conditioning" of dentin or enamel prior to the application of a single solution bonding formulation of the present invention refers to removal of loose dental debris or dead tissue and mineral from the exposed dentin surface to a depth of about 10 μm. Conditioning methods are well known to those skilled in the art. For example, etching with phosphoric acid can be used. Alternatively, a polymerizable conditioner can be used as described by Dickens et al., J. Dent. Res. 77:202 (1996). See also U.S. Pat. Nos. 6,001,897 and 6,187,838.

Various abbreviations used herein are described below. Calcium phosphate cement (CPC) is a mixture of dicalcium phosphate anhydrous (DCPA) and tetracalcium phosphate (TTCP) or dicalcium phosphate dihydrate (DCPD) and tetracalcium phosphate (TTCP). When the DCPA and TTCP or DCPD and TTCP are provided in sufficient amount, hydroxyapatite forms when water is added to the mixture.

The formula for amorphous calcium phosphate (ACP) is $Ca_3(PO_4)_{1.8}(HPO_4)_{0.2}$.

The following structures of compounds correspond to their associated abbreviations noted below:

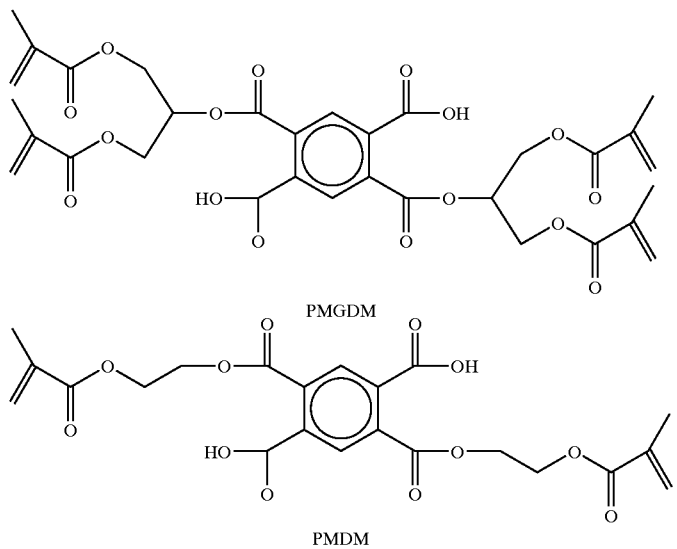

PMGDM

PMDM

-continued
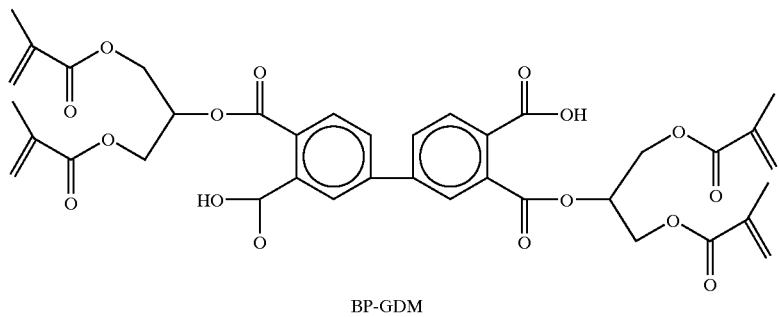
BP-GDM
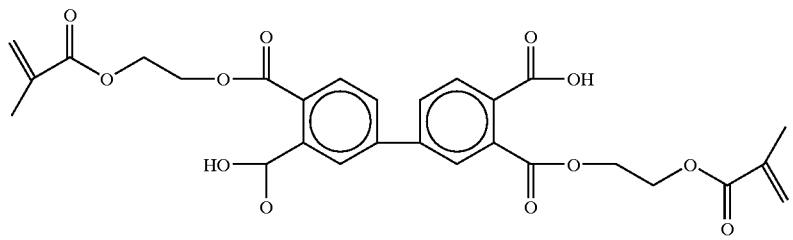
BP-HEMA
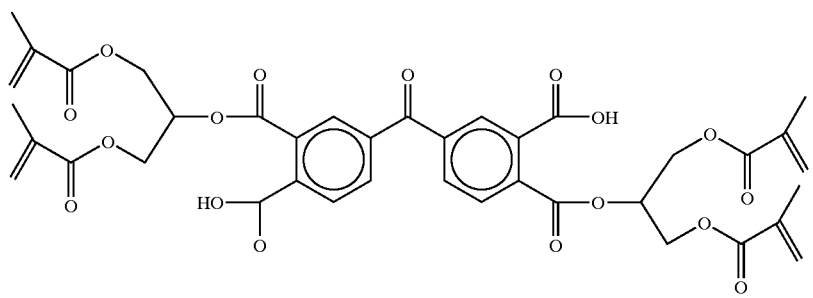
BPh-GDM
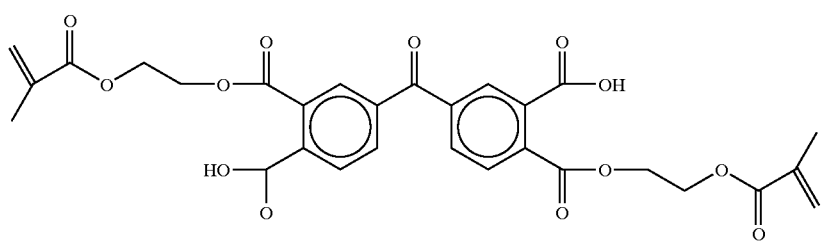
BPh-HEMA
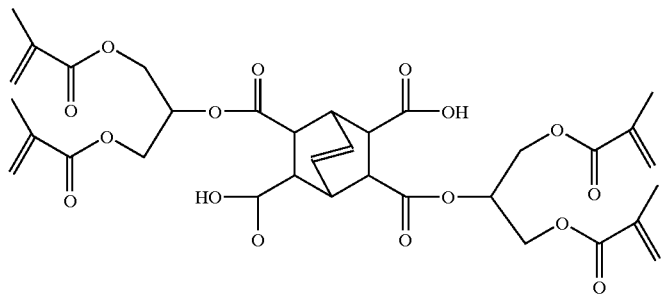
BCOE-GDM -continued
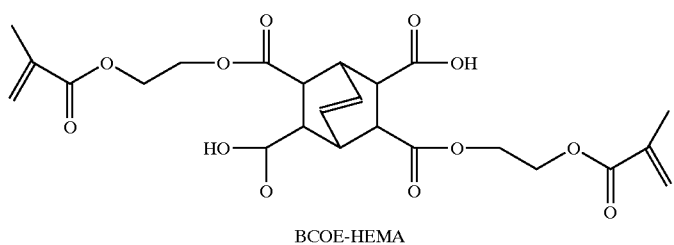
BCOE-HEMA
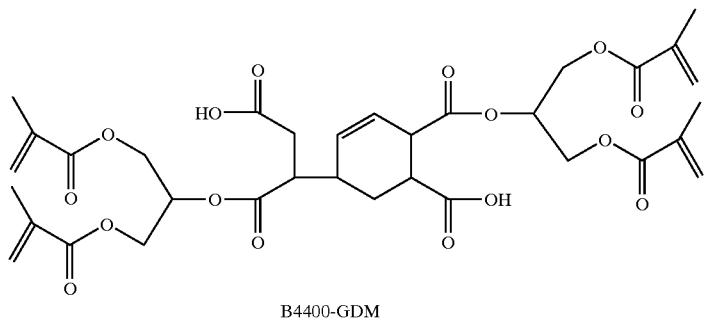
B4400-GDM
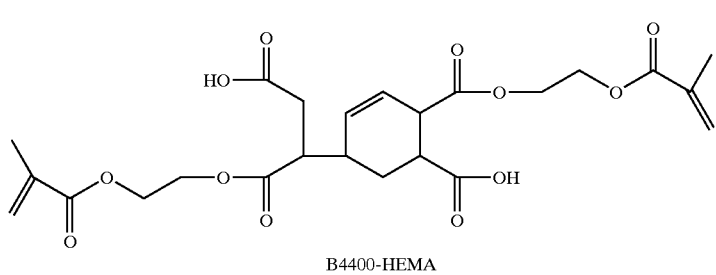
B4400-HEMA
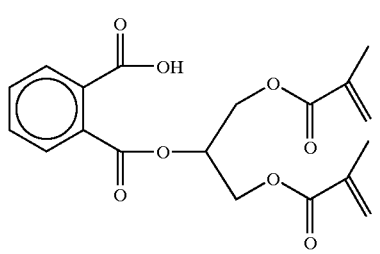
PhTh-GDM
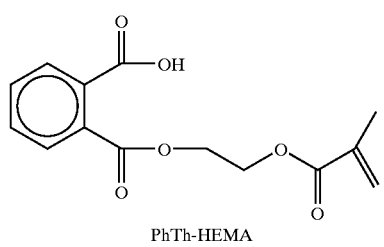
PhTh-HEMA
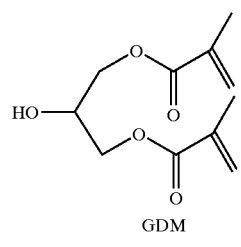
GDM
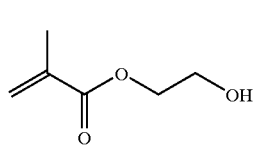
HEMA
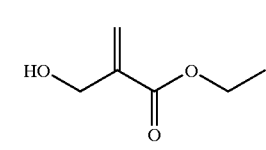
EHMA
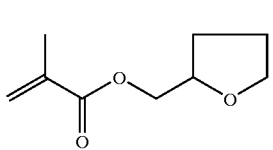
THFMA
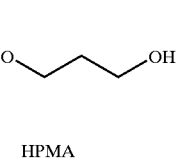
HPMA
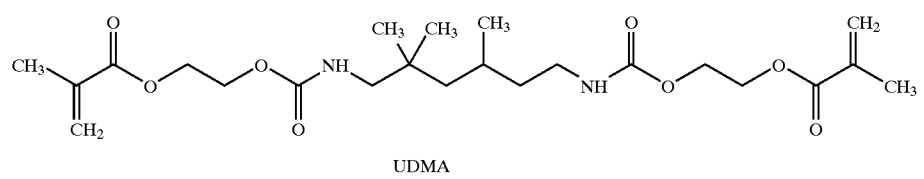
UDMA

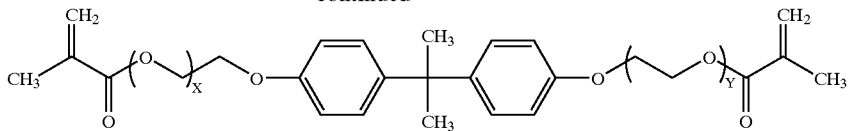

EMPADMA

X and Y are independently integers wherein X=1, 2, 3, 4, or 5, preferably X=2, 3, or 4; and wherein Y=1, 2, 3, 4, or 5, preferably Y=3, 4, or 5.

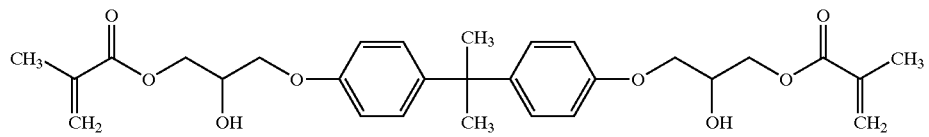

Bis-GMA

The following compound abbreviations correspond to their associated names set forth below:

| | |
|---|---|
| GDM | glycerol dimethacrylate |
| HEMA | 2-hydroxyethylmethacrylate |
| EHMA | ethyl-α-hydroxy methacrylate |
| THFM | tetrahydrofurfuryl methacrylate |
| HPMA | hydroxypropyl methacrylate |
| UDMA | urethane dimethacrylate |
| EBPADMA | ethoxylated bisphenol A dimethacrylate |
| Bis-GMA | 2,2'-bis[p(2'-hydroxy-3'-methacryloxypropoxy)phenylene]propane |
| PMGDM | Pyromellitic dianhydride GDM adduct |
| PMDM | Pyromellitic dianhydride HEMA adduct |
| BP-GDM | Biphenyl dianhydride GDM adduct |
| BP-HEMA | Biphenyl dianhydride HEMA adduct |
| BPh-GDM | Benzophenone-3,3',4,4'-tetracarboxylic dianhydride GDM adduct |
| BPh-HEMA | Benzophenone-3,3',4,4'-tetracarboxylic dianhydride HEMA adduct |
| BCOE-GDM | Bicyclo[2.2.2]oct-7-ene-2,3,5,6-tetracarboxylic dianhydride GDM adduct |
| BCOE-HEMA | Bicyclo[2.2.2]oct-7-ene-2,3,5,6-tetracarboxylic dianhydride HEMA adduct |
| B4400-GDM | 5-(2,5dioxotetrahydro-3-furanyl)-3-cyclohexene-1,2-dicarboxylic anhydride GDM adduct |
| B4400-HEMA | 5-(2,5dioxotetrahydro-3-furanyl)-3-cyclohexene-1,2-dicarboxylic anhydride HEMA adduct |
| PhTh-GDM | Phthalic anhydride GDM adduct |
| PhTh-HEMA | Phthalic anhydride HEMA adduct |

According to one embodiment of the invention, a single solution bonding formulation for dental applications is provided. Such formulation comprises:

(a) a plurality of a self-polymerizable polyvinyl acidic monomer or a plurality of at least two different polyrnerizable polyvinyl acidic monomers, (b) a calcium phosphate filler, (c) at least one polymerization photoinitiator, (d) optionally, an accelerator, (e) optionally, a solvent, and (f) optionally, a fluoride additive.

The above-noted formulation is a single solution bonding formulation (i.e., it does not require storage in two or more parts requiring mixing of the parts prior to application).

Additionally, the above-noted single solution bonding formulation is free of ascorbic acid or its derivatives recited in U.S. Pat. No. 4,918,136 to Kawaguchi.

Suitable polymerization monomers may be either a plurality of the same self-polymerizable polyvinyl acidic monomers or at least two different polymerizable polyvinyl acidic monomers sufficient to form a crosslinked matrix suitable at least for dental applications (e.g., repair and/or restoration of enamel and/or dentin). Such polymerizable polyvinyl acidic monomers should be compatible with mammalian dental tissues including, but not limited to, enamel, dentin and/or pulp. Examples of such polymerizable polyvinyl acidic monomers include, but are not limited to, methacrylate polyvinyl acidic monomers. Additional methacrylate monomers may be added to the polyvinyl acidic monomers. Such additive methacrylate monomers may include, but are not limited to, acidic methacrylate monomers, non-acidic methacrylate monomers and combinations thereof.

Typical polyvinyl acidic methacrylate monomers include, but are not limited to, pyromellitic dianhydride GDM adduct (PMGDM), pyromellitic dianhydride HEMA adduct (PMDM), biphenyl dianhydride GDM adduct (BP-GDM), biphenyl dianhydride HEMA adduct (BP-HEMA), benzophenone-3,3',4,4'-tetracarboxylic dianhydride GDM adduct (BPh-GDM), benzophenone-3,3',4,4'-tetracarboxylic dianhydride HEMA adduct (BPh-HEMA), bicyclo[2.2.2]oct-7-ene-2,3,5,6-tetracarboxylic dianhydride GDM adduct (BCOE-GDM), bicyclo[2.2.2]oct-7-ene-2,3,5,6-tetracarboxylic dianhydride HEMA adduct (BCOE-HEMA), 5-(2,5dioxotetrahydro-3-furanyl)-3-cyclohexene-1,2-dicarboxylic anhydride GDM adduct (B4400-GDM), 5-(2,5dioxotetrahydro-3-furanyl)-3-cyclohexene-1,2-dicarboxylic anhydride HEMA adduct (B4400-HEMA), phthalic anhydride GDM adduct (PhTh-GDM), and combinations thereof. Preferred polyvinyl acidic methacrylate monomers include, but are not limited to, PMGDM, BP-GDM, PMDM, BPh-HEMA, and combinations thereof. More preferred polyvinyl acidic methacrylate monomers include, but are not limited to, PMGDM, BP-GDM, PMDM, and combinations thereof. Even more preferred polyvinyl acidic methacrylate monomers include, but are not limited to, PMGDM BP-GDM, and combinations thereof.

Typical additive methacrylate monomers include, but are not limited to, 2-hydroxyethylmethacrylate (HEMA), glycerol dimethacrylate (GDM), ethyl-α-hydroxy methacrylate (EHMA), tetrahydrofurfuryl methacrylate (THFM), hydroxypropyl methacrylate (HPMA), urethane dimethacrylate (UDMA), ethoxylated bisphenol A dimethacrylate (EBPADMA), 2,2'-bis[p-(2'-hydroxy-3'-methacryloxypropoxy)phenylene]-propane (Bis-GMA), and combinations thereof. Preferred additive methacrylate monomers include, but are not limited to, HEMA, GDM, EHMA, HPMA, Bis-GMA, and combinations thereof. More preferred additive methacrylate monomers include, but are not limited to, HEMA, EHMA, HPMA, and combinations thereof.

Typically, the above-noted polyvinyl acidic methacrylate monomer(s) are provided in an amount from about 2% to about 95% by weight of the monomer(s) based on a total weight of the single solution bonding formulation. Preferred amounts are from about 20% to about 80% by weight of the polyvinyl acidic methacrylate monomer(s) based on a total weight of the single solution bonding formulation. More preferred amounts are from about 30% to about 80% by weight of the polyvinyl acidic methacrylate monomer(s) based on a total weight of the single solution bonding formulation. Even more preferred amounts are from about 30% to about 60% by weight of the polyvinyl acidic methacrylate monomer(s) based on a total weight of the single solution bonding formulation. Yet even more preferred amounts are from about 30% to about 45% by weight of the polyvinyl acidic methacrylate monomer(s) based on a total weight of the single solution bonding formulation.

The amount of the additive methacrylate monomers may vary from about 0% to about 50%, or from 1% to about 50%, preferably from about 5% to about 40%, more preferably from about 5% to about 30%, even more preferably from about 7% to about 25%, yet even more preferably from about 9% to about 20%, and still more preferably from about 10% to about 15% by weight, respectively, based on a total weight of the single solution bonding formulation.

According to another embodiment of the invention, a calcium phosphate filler sufficient to release calcium ions, and phosphate ions, and optionally a fluoride additive sufficient to release fluoride ions, or combinations thereof is provided in the single solution bonding formulation. Preferably the single solution bonding formulation comprises an amount of the calcium phosphate filler and the fluoride additive sufficient to allow in situ formation of fluorapatite and/or hydroxyapatite in the underlying and/or surrounding enamel and/or dentin. Typical calcium phosphate fillers suitable for use with the present invention include, but are not limited to, dicalcium phosphate anhydrous (DCPA), silanated dicalcium phosphate anhydrous, dicalcium phosphate dihydrate (DCPD), silanated dicalcium phosphate dihydrate, calcium phosphate cement (CPC), silanated calcium phosphate cement, tetracalcium phosphate (TTCP), amorphous calcium phosphate (ACP), and a combination thereof. Preferred calcium phosphate fillers include, but are not limited to, CPC, DCPA, DCPD, TTCP, ACP, and combinations thereof. More preferred calcium phosphate fillers include, but are not limited to, CPC, DCPA, DCPD, ACP, and combinations thereof.

Typically, the calcium phosphate filler is provided in an amount from about 2.5% to about 50% by weight based on a total weight of the single solution bonding formulation. Preferred amounts are from about 5% to about 40% by weight of the calcium phosphate filler based on a total weight of the single solution bonding formulation. More preferred amounts are from about 10% to about 30% by weight of the calcium phosphate filler based on a total weight of the single solution bonding formulation. Even more preferred amounts are from about 15% to about 25% by weight of the calcium phosphate filler based on a total weight of the single solution bonding formulation. Yet even more preferred amounts are from about 20% to about 25% by weight of the calcium phosphate filler based on a total weight of the single solution bonding formulation.

The dicalcium phosphate anhydrous is usually provided in an amount from about 1% to about 99% by weight and the tetracalcium phosphate is provided in an amount from about 99% to about 1% by weight based on a total weight of the calcium phosphate cement. Preferred amounts are from about 10% to about 90% by weight of the dicalcium phosphate anhydrous and from about 90% to about 10% by weight of the tetracalcium phosphate based on a total weight of the calcium phosphate cement. More preferred amounts are from about 20% to about 80% by weight of the dicalcium phosphate anhydrous from about 80% to about 20% by weight of the tetracalcium phosphate based on a total weight of the calcium phosphate cement. Even more preferred amounts are from about 20% to about 50% by weight of the dicalcium phosphate anhydrous and from about 80% to about 50% by weight of the tetracalcium phosphate based on a total weight of the calcium phosphate cement. Yet even more preferred amounts are from about 20% to about 40% by weight of the dicalcium phosphate anhydrous and from about 80% to about 60% by weight of the tetracalcium phosphate based on a total weight of the calcium phosphate cement. Yet even more preferred amounts are about 27% by weight of the dicalcium phosphate anhydrous and about 73% by weight of the tetracalcium phosphate based on a total weight of the calcium phosphate cement.

The dicalcium phosphate dihydrate is usually provided in an amount from about 30% to about 70% by weight and the tetracalcium phosphate is provided in an amount from about 70% to about 30% by weight based on a total weight of the calcium phosphate cement. Preferred amounts are about 32% by weight of the dicalcium phosphate dihydrate and about 68% by weight of the tetracalcium phosphate based on a total weight of the calcium phosphate cement.

Typical silanating agents for the above-noted silanated fillers include, but are not limited to, methacryloylpropoxy-trimethoxysilane, methacryloylpropoxy-triethoxysilane, vinyl-trimethoxysilane, and vinyl-triethoxysilane. The silanating agent is typically provided in an amount from about 0.5% to about 10% by weight based on a total weight of the calcium phosphate filler or on the total weight of calcium phosphate and inert filler. Preferred amounts are from about 0.5% to about 7% by weight of the silanating agent based on a total weight of the calcium phosphate filler or on the total weight of calcium phosphate and inert filler.

According to another embodiment, the calcium phosphate filler may optionally further comprise an inert filler. Typical inert fillers suitable for use with the present invention include, but are not limited to, microfine silica, nanofiller, and combinations thereof.

The microfine silica is typically provided in an amount from about 20% to about 40% by weight based on a total weight of the filler. Preferred amounts are from about 25% to about 40% by weight of the microfine silica based on a total weight of the filler. More preferred amounts are from about 30% to about 40% by weight of the microfine silica based on a total weight of the filler.

Typically, the nanofiller is provided in an amount from about 20% to about 40% by weight based on a total weight of the filler. Preferred amounts are from about 30% to about 40% by weight of the nanofiller based on a total weight of the filler.

According to another embodiment, at least one polymerization photoinitiator (preferably at least two) sufficient to photoinitiate polymerization of the polyvinyl acidic monomers is provided. Typical polymerization photoinitiators suitable for use with the present invention include, but are not limited to, visible light activated photoinitiators, ultraviolet light activated photoinitiators and combinations thereof According to another embodiment of the invention, a visible light activated photoinitiator with an activation wavelength compatible with dental applications is provided.

Typical visible light activated photoinitiators suitable for use with the present invention include, but are not limited to, camphorquinone, benzil (CAS Registry Number 134-81-6), mono- and bis-(acylphosphine oxides), derivatives and combinations thereof.

Visible light photoinitiator activation wavelengths for polymerization of the polyvinyl acidic monomers are usually from about 380 to about 590 nm. Preferred activation wavelengths are from about 380 to about 550 nm. More preferred activation wavelengths are from about 400 to about 500 nm. Even more preferred activation wavelengths are from 420 to about 490 nm. Yet even more preferred activation wavelengths are from 420 to about 480 nm.

According to another embodiment of the invention, a visible light activated photoinitiator with an activation time compatible with dental applications is provided. Typically, the activation time is from about 3 seconds to about 2 minutes. Preferred activation time is from about 3 seconds to about 1 minute. More preferred activation time is from about 3 seconds to about 50 seconds. Even more preferred activation time is from about 3 seconds to about 40 seconds. Yet even more preferred activation time is from about 3 seconds to about 30 seconds.

Ultraviolet light activated photoinitiators suitable for use with the present invention include, but are not limited to, mono phosphineoxides, bis phosphineoxides, 2,2-dimethoxy-2-phenylacetophenone, derivatives and combinations thereof. Preferred ultraviolet light activated photoinitiators include, but are not limited to, mono phosphineoxides, bis phosphineoxides, and combinations thereof.

According to another embodiment of the invention an ultraviolet light activated photoinitiator with an activation time compatible with dental applications is provided. Typically, the activation time is from about 3 seconds to about 2 minutes. Preferred activation time is from about 3 seconds to about 1 minute. More preferred activation time is from about 3 seconds to about 50 seconds. Even more preferred activation time is from about 3 seconds to about 40 seconds. Yet even more preferred activation time is from about 3 seconds to about 30 seconds.

Typically, at least one polymerization photoinitiator (preferably, at least two) is provided in an amount from about 0.2% to about 2% by weight based on a total weight of the single solution bonding formulation. Preferred amounts are from about 0.3% to about 1.7% by weight of the polymerization photoinitiator based on a total weight of the single solution bonding formulation. More preferred amounts are from about 0.4% to about 1.7% by weight of the polymerization photoinitiator based on a total weight of the single solution bonding formulation. Even more preferred amounts are from about 0.4% to about 1.6% by weight of the polymerization photoinitiator based on a total weight of the single solution bonding formulation.

According to another embodiment of the invention, an optional accelerator compatible with dental applications is provided. Typical accelerators suitable for use with the present invention include, but are not limited to, tertiary amines such as $R_1R_2$-N-$R_3$-X wherein $R_1$ and $R_2$ may be the same or different and selected from the group consisting of an alkyl or alkanol, wherein $R_3$ is selected from the group consisting of aromatic and aliphatic, and wherein X is an electron withdrawing group.

The accelerator suitable for use with the present invention is usually provided in an amount from about 0% to about 1% by weight based on a total weight of the single solution bonding formulation. Preferred amounts are from about 0.1% to about 0.8% by weight of the accelerator based on a total weight of the single solution bonding formulation. More preferred amounts are from about 0.2% to about 0.6% by weight of the accelerator based on a total weight of the single solution bonding formulation. Even more preferred amounts are from about 0.4% to about 0.6% by weight of the accelerator based on a total weight of the single solution bonding formulation.

According to another embodiment, an optional solvent compatible with mammalian tissue is provided. Typical solvents suitable for use with the present invention include, but are not limited to, acetone, ethanol, water, tetrahydrofuran and mixtures thereof. Preferred solvents include, but are not limited to, acetone, ethanol, water, and mixtures thereof.

The solvent is typically provided in an amount from about 0% to about 80% by weight of the solvent based on a total weight of the single solution bonding formulation. Preferred amounts are from about 20% to about 80% by weight of the solvent based on a total weight of the single solution bonding formulation. More preferred amounts are from about 30% to about 60% by weight of the solvent based on a total weight of the single solution bonding formulation. Even more preferred amounts are from about 40% to about 55% by weight of the solvent based on a total weight of the single solution bonding formulation. Yet even more preferred amounts. are from about 42% to about 52% by weight of the solvent based on a total weight of the single solution bonding formulation.

Typically, for an acetone/ethanol solvent system, the solvent comprises about 25% by weight acetone and about 75% by weight ethanol based on the total weight of the solvent. Preferably, the solvent comprises about 50% by weight acetone and about 50% by weight ethanol based on the total weight of the solvent. More preferably, the solvent comprises about 75% by weight acetone and about 25% by weight ethanol based on the total weight of the solvent.

For a water/ethanol solvent system, the solvent typically comprises about 7% by weight water and about 93% by weight ethanol based on the total weight of the solvent. Preferably, the solvent comprises about 3% by weight water and about 97% by weight ethanol based on the total weight of the solvent. More preferably, the solvent comprises about 1% by weight water about 99% by weight ethanol based on the total weight of the solvent.

According to another embodiment, typically, a shear bond strength of at least about 28 MPa is achieved when the single solution bonding formulation of the present invention is bonded to sound dentin in accordance with the present invention. Typical dentin bond strengths are from about 28 MPa to about 37 MPa when bonded to normal or carious dentin. The method used to measure the shear bond strength is well known to those skilled in the art. One such method is described below. Caries-free and carious human molars are mounted in plastic holding rings and sectioned horizontally through the crown with a low-speed diamond saw, exposing a flat dentin surface perpendicular to the long axis of the tooth. The caries-free molars are demineralized in a demineralizing solution at pH of 4.8 for 48 hours. The teeth are subsequently conditioned with 37% phosphoric acid or P-etch, a polymerizable conditioner, rinsed with water and treated as follows: each tooth receives two coats of bonding agent followed by a 10 second light cure. One point five mm thick Teflon-coated steel irises with internal diameters of about four mm are placed in a positioning device on the dentin surface and a composite resin is inserted and light cured for one minute. The irises containing the composite resin, which is bonded to the dentin surface, are sheared off with a knife-edged blade at a crosshead speed of 0.5 mm/min using a universal testing machine (Instron Corporation). The shear bond strength is calculated by dividing the maximum load at fracture by the bond area.

According to another embodiment of the invention, after polymerization of the monomer, the polymerized single solution bonding formulation permits diffusion into the surrounding and/or underlying dental structures of components including, but not limited to, calcium, phosphate, fluoride and combinations thereof (e.g., calcium and phosphate; calcium and fluoride; and calcium, phosphate and fluoride) sufficient to form fluorapatite and/or hydroxyapatite.

According to another embodiment of the invention, a polymerized matrix able to release calcium into the underlying or surrounding enamel, dentin, or pulp is formed. Typical calcium diffusion rates (measured as described in Example 5) are from about 10 $\mu molL^{-1}day^{-1}$ to about 30 $\mu molL^{-1}day^{-1}$.

According to another embodiment of the invention, a polymerized matrix able to release phosphate into the underlying or surrounding enamel, dentin, or pulp is formed. Typical phosphate diffusion rates (measured as described in Example 5) are from about 65 $\mu molL^{-1}day^{-1}$ to about 135 $\mu molL^{-1}day^{-1}$.

According to another embodiment of the invention, a polymerized matrix able to release fluoride into the underlying or surrounding enamel, dentin, or pulp is formed. Typical fluoride diffusion rates (measured as described in Example 5) are from about 10 $\mu molL^{-1}day^{-1}$ to about 45 $\mu molL^{-1}day^{-1}$.

According to another embodiment of the invention, a single solution bonding formulation with a pH compatible with dental applications is provided.

According to another embodiment of the invention, the single solution bonding formulation optionally further comprises a fluoride additive component. Typically, such fluoride additive components suitable for use with the present invention include, but are not limited to, sodium hexafluorosilicate, sodium hexafluorophosphate, sodium hexafluoroantimonate, sodium fluoride, sodium monofluor phosphate, potassium hexafluorosilicate, potassium hexafluorophosphate, potassium hexafluoroantimonate, and combinations thereof. Preferred fluoride-containing components include, but are not limited to, sodium hexafluorosilicate, sodium hexafluoroantimonate, potassium hexafluorosilicate, potassium hexafluoroantimonate, and combinations thereof.

The fluoride additive component is typically provided in an amount from about 0% to about 2% by weight or from about 0.2% to about 2% by weight, respectively, based on a total weight of the single solution bonding formulation. Preferred amounts are from about 0.4% to about 1.8% by weight of the fluoride additive component based on a total weight of the single solution bonding formulation. More preferred amounts are from about 0.6% to about 1.5% by weight of the fluoride additive component based on a total weight of the single solution bonding formulation. Even more preferred amounts are from about 0.8% to about 1.2% by weight of the fluoride additive component based on a total weight of the single solution bonding formulation. Yet even more preferred amounts are from about 0.9% to about 1% by weight of the fluoride additive component based on a total weight of the single solution bonding formulation.

According to another embodiment of the invention, the single solution bonding formulation is provided in a pharmaceutical form compatible with dental applications. Examples of such forms include, but are not limited to, a paste, a creme, a gel, a solution, an emulsion, a dispersion and a suspension.

Preferred forms include, but are not limited to, a paste, gel, a solution, and a dispersion. More preferred forms include, but are not limited to, a solution and a dispersion.

According to another embodiment of the invention, a method to prepare a single solution bonding formulation is provided. Such method comprises the step of:

a) mixing:
aa) a plurality of a self-polymerizable polyvinyl acidic monomer or a plurality of at least two different polymerizable polyvinyl acidic monomers,
bb) a calcium phosphate filler,
cc) at least one polymerization photoinitiator,
dd) optionally, an accelerator,
ee) optionally, a solvent, and
ff) optionally, a fluoride additive.

According to another embodiment of the invention, a method to treat enamel, dentin, or pulp is provided. Such a method comprises the steps of:

a) applying to the enamel, dentin, or exposed pulp a single solution bonding formulation, and b) then exposing the applied formulation to light sufficient to polymerize the formulation.

According to another embodiment of the invention, a method to treat enamel, dentin, or pulp is provided. Such a method optionally further comprises conditioning the enamel or dentin before applying the single solution bonding formulation of the present invention. The conditioning step further comprises exposing the enamel or dentin to a conditioning solution, and then washing away the conditioning solution. Thereafter, the single solution bonding formulation is applied to the conditioned dental structure.

According to another embodiment of the invention, the enamel, dentin, and/or pulp preferably belong to a mammal such as a human or a veterinary animal (e.g., domesticated animals such as show animals, dogs, cats, etc.).

All patents, journal articles, abstracts and any other references cited in this application are incorporated herein by reference in their entirety.

The following examples are provided for illustrative purposes only and are not intended to limit the scope of the present invention.

METHODS USED IN THE EXAMPLES

A two factorial design was used to assess the extent to which a resin-based calcium phosphate cement (CP-RC) restored the mineral content of demineralized dentin when placed directly on dentin or when placed over a bonding agent (BA). Two cavities, 3 mm in diameter and 1 mm deep, were drilled into the occlusal dentin surface of 16 extracted human molars. The teeth were then exposed to a demineralizing solution (0.075 mol/L glacial acetic acid, 0.002 mol/L $Ca^{2+}$ from $CaCl_2$, and 0.002 mol/L $PO_4^{3-}$ from KH$_2$PO$_4$) for 48 h and divided into two groups: one half was treated as is, the other half was treated with a calcium phosphate-free bonding agent (BA), which was light cured before inserting the cements. One of the two cavities was filled with a composite resin as a non-remineralizing control, the other received one of the experimental treatments: CP-RC, CP-RC+fluoride (F-CP-RC), BA with CP-RC, BA with F-CP-RC. The teeth were stored in artificial saliva at 37° C. for 6 weeks, after which ≈180 µm thick cross sections were cut. The mineral content under the restorations was analyzed by digital radiography comparing the mineral density under the calcium phosphate filler to that under the composite resin, which served as an internal control. The mean percent remineralization over the control treatment±standard deviation was for CP-RC 39±14, F-CP-RC 37±18, BA/CP-RC 23±13, BA/F-CP-RC 14±7, respectively. Two-way ANOVA and Tukey test (p<0.001) showed a significant effect from the presence of the bonding agent, which may have retarded the diffusion of calcium and phosphate ions from the calcium phosphate filler into the underlying dental structures. Alternatively, the bonding agent bound the calcium ions and prevented the same from diffusing into the surrounding dental structures. Incorporating fluoride in the cement did not affect the remineralization significantly (p>0.05).

These experiments illustrated that the remineralization from the calcium phosphate filler was significantly compromised by the presence of a bonding agent.

Thus, a single solution bonding formulation capable of remineralizing the underlying dental structures (e.g., enamel or dentin) or stimulating the repair of the exposed pulp was designed by incorporating the calcium phosphate filler directly into the bonding agent. Bond strengths of those formulations were compared to those formulations not containing calcium phosphate fillers. The basic composition of an exemplary single solution bonding formulation of the present invention comprises pyromellitic glycerol dimethacrylate (PMGDM), 2-hydroxyethyl methacrylate (HEMA), camphorquinone, a tertiary amine as photoinitiator and co-catalyst, acetone at various levels and various calcium phosphate fillers at a weight fraction of 20% based on the total weight of the single solution bonding formulation. Exemplary calcium phosphate fillers used were:

1) DCPA—dicalcium phosphate anhydrous;
2) DCPA silanated with methacryloylpropoxytriethoxysilane;
3) DCPA mixed with microfine silica at a weight ratio of 0.5 parts each;
4) CPC, a mixture of 0.27 parts DCPA and 0.73 parts TTCP (tetracalcium phosphate);
5) CPC silanated with methacryloylpropoxytriethoxysilane;
6) CPC mixed with microfine silica (0.5 parts each).

Example 1

Shear bond strengths to dentin mediated by unsilanated and silanated (e.g., DCPA and CPC versus silanated DCPA and silanated CPC) single solution bonding formulations were evaluated as described above after phosphoric acid conditioning. Results are summarized in Table 1. The mean and standard deviations are reported, n indicates the number of specimens tested.

TABLE 1

Comparison of unsilanized to silanized DCPA or CPC fillers in the single solution bonding formulations (46% acetone) on demineralized dentin.

|  | unsilanized | | | silanized | | |
| --- | --- | --- | --- | --- | --- | --- |
|  | mean | sd | n | mean | sd | n |
| DCPA | 34.2 | 5.9 | 4 | 26.5 | 3.3 | 6 |
| CPC | 29.7 | 6.3 | 4 | 27.7 | 1.5 | 4 |

Example 2

The same procedure as in Example 1 was followed except that the single solution bonding formulation contained a calcium phosphate filler (filled) or did not contain the same (unfilled). Shear bond strength of the filled and unfilled single solution bonding formulations on normal and demineralized dentin were compared. Results are summarized in Table 2.

TABLE 2

Shear bond strength to normal and demineralized dentin with DCPA/silica.

| Normal dentin | | | | | | | Demineralized dentin | | | | | | |
| --- | --- | --- | --- | --- | --- | --- | --- | --- | --- | --- | --- | --- | --- |
| | unfilled | | | filled | | | | unfilled | | | filled | | |
| acetone | mean | sd | n | mean | sd | n | acetone | mean | sd | n | mean | sd | n |
| 33% | 38.9 | 5.6 | 4 | 28.8 | 4.3 | 4 | 33% | 23.0 | 5.1 | 3 | 20.8 | 5.8 | 4 |
| 46% | 37.1 | 2.0 | 4 | 35.2 | 8.5 | 4 | 46% | 29.6 | 6.3 | 3 | 23.2 | 2.8 | 3 |
| 57% | 35.0 | 1.5 | 4 | 28.2 | 5.3 | 4 | 57% | 30.4 | 6.2 | 3 | 26.2 | 2.0 | 4 | n = number of specimens. Since this was an unbalanced design, 2-way ANOVA was performed for normal dentin and showed no effect from the acetone concentration but tested significant for the presence of filler, p < 0.05. On demineralized dentin, the acetone content was found to be significant (p < 0.05) but the filler level was not (p > 0.05).
unfilled = no calcium phosphate filler
filled = contains calcium phosphate filler

Example 3

The same procedure as in Example 1 was followed. The bond strength on demineralized dentin was determined using various calcium phosphate fillers and different etching techniques on demineralized demineralized dentin.

Results are summarized in Table 3.

TABLE 3

Compare various fillers in the single solution bonding formulation on demineralized dentin.

| Etchant | Solvent | Calcium Phosphate Filler | mean | sd | Number of specimens |
|---|---|---|---|---|---|
| P-etch | 46% acetone | #3 (DCPA/silica) | 29.7 | 4.2 | 3 |
| $H_3PO_4$ etch | 46% acetone | #3 (DCPA/silica) | 24.8 | 3.6 | 4 |
| $H_3PO_4$ etch | 46% acetone | #4 (CPC) | 29.7 | 6.3 | 4 |
| $H_3PO_4$ etch | 46% acetone | #2 (DCPA) | 25.0 | 11.6 | 4 |
| $H_3PO_4$ etch | 46% acetone | #6 (CPC/silica) | 23.9 | 2.3 | 4 |

Addition of silica led to significantly lower bond strengths; 1-way ANOVA; Tukey's multiple comparison; $p < 0.05$.

tion had significantly ($p<0.001$) smaller lesion depth ($115$ $\mu m \pm 22$ $\mu m$ for the single solution bonding formulation vs. $153 \pm 38$ $\mu m$ for the unfilled bonding resin) and a smaller loss in mineral density ($46 \pm 13$ $\mu m$ vs. $64 \pm 13$ $\mu m$) than the teeth treated with the unfilled bonding resin. The loss in mineral density is in relative comparison to the unaltered dentin and resulted from demineralizing the teeth prior to bonding. Thus, a smaller loss in mineral density and in lesion depth indicates that some mineral from the single solution bonding formulation may have diffused into the mineral-depleted dentin surface.

Example 4

The same procedure as in Example 1 was followed except that the single solution bonding formulation contained a calcium phosphate filler (filled) or did not contain the same (unfilled). The bond strength on normal dentin, carious dentin and demineralized dentin was determined using different etching techniques. Results are summarized in Table 4.

TABLE 4

Compare 2 conditioners on normal, carious or demineralized dentin with unfilled or filled single solution bonding formulation.

| | Normal dentin | | | | | | Carious dentin | | | | | | Demineralized dentin | | | | | |
|---|---|---|---|---|---|---|---|---|---|---|---|---|---|---|---|---|---|---|
| | unfilled | | | filled* | | | unfilled | | | filled | | | unfilled | | | filled | | |
| | mean | sd | n | mean | sd | n | mean | sd | n | mean | sd | n | mean | sd | n | mean | sd | n |
| $H_3PO_4$ | 38.7 | 2.9 | 6 | 33.2 | 3.3 | 4 | 36.5 | 6.5 | 4 | 23.5 | 3.1 | 4 | 29.6 | 6.3 | 4 | 26.5 | 3.3 | 6 |
| P-etch | 33.0 | 5.3 | 4 | 36.9 | 4.8 | 4 | 33.3 | 4.5 | 4 | 27.0 | 4.7 | 4 | 33.3 | 4.5 | 4 | 29.2 | 4.0 | 4 |

*Filler #2 (silanated DCPA); 3 way ANOVA detected no significant difference for the acid conditioners used ($p > 0.05$). The interaction between conditioner and filler was significant ($p = 0.009$). There were also a significant difference for dentin substrate and filler level and a significant interaction between dentin substrate and filler. ($p < 0.05$).

The effect of the demineralization procedure and the subsequent coating with either an unfilled bonding agent or the single solution bonding formulation, was assessed by digital image analysis. For the image analysis, six teeth had been demineralized for 48 h in a demineralizing solution at pH 4.8. Three teeth were then bonded with the unfilled bonding resin and three teeth were bonded with the filled bonding system (Filler # 3; data in Table 2). After debonding, approximately 180 $\mu m$ thick transverse sections through the bonded areas were prepared. Microradiographs of these sections were obtained as described by Chow et al. (1991; 1992). Briefly, three to four images of one tooth section were digitally captured with special software and a digital camera attached to a microscope. Of each sample an area located in the sound portion of the dentin was chosen as the internal reference. The mineral density of the demineralized region adjacent to tooth surface and the reference area were obtained. These data were converted into a mineral content profile of the captured image as a function of distance from dentin surface and produced values for the average mineral loss in the deminemlized dentin surface and the extent of the lesion depth in micrometer.

The imaging analysis showed that the teeth treated with the single solution bonding formulation of the present inven- The results of these experiments show that high bond strengths, especially with the polymerizable etchant, can be obtained when bonding to demineralized or carious dentin, with single solution bonding formulation of the present invention.

Example 5

Calcium, total phosphate, and fluoride release was determined on specimens prepared from three single solution bonding agents containing different calcium phosphate fillers after solvent removal. For the fluoride, calcium and phosphate analyses, six disks, 15 mm in diameter and 1 mm high, were prepared from the bonding agents after the acetone had been removed. The specimens were cured in Teflon molds under the light guides of three dental curing lights (MAX, Dentsply, Int.). A piece of fishing line of known weight was inserted to allow free suspension of the specimen in solution. After removing the specimen from the mold, the weight of each specimen was recorded. Three disks of each formulation were placed in 10 ml saliva-like solution (SLS). The solutions containing the specimens were stored at 37° C.

Figure 2:
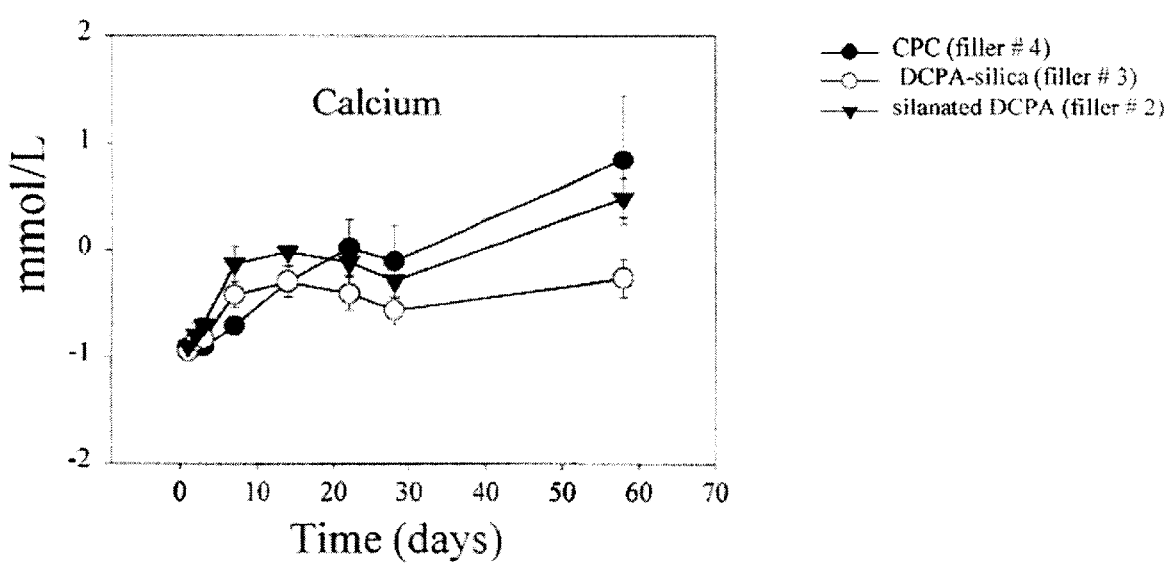
FIG. 2 is a plot of calcium ion release (mmol/L) versus time wherein the calcium ion release is from a single solution bonding formulation. The total concentration of calcium ions released was measured with spectrophotometric methods using known standards and calibration techniques (Vogel et al., Caries Red 17:23–31, 1983), and substituting concentrated formic acid for glacial acetic acid.
Figure 3:
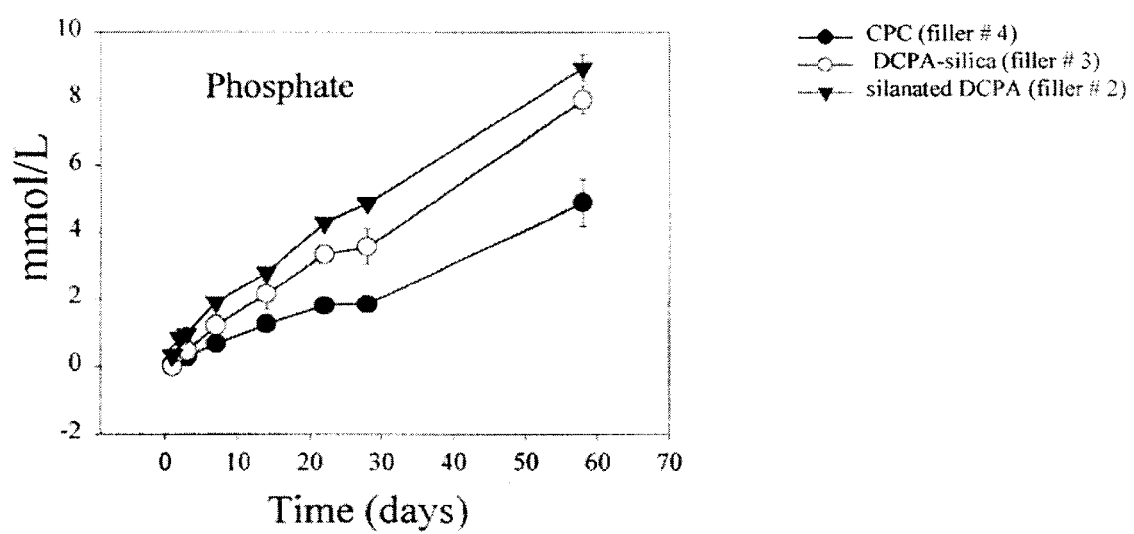
FIG. 3 is a plot of phosphate ion release (mmol/L) versus time wherein the phosphate ion release is from a single solution bonding formulation. The total concentration of phosphate ions released was measured with spectrophotometric methods using known standards and calibration techniques (Vogel et al., 1983), and substituting potassium hydroxide for tetrabutyl ammonium hydroxide.

At given time intervals, 1.5 ml of the storage solution was removed for analysis and replaced by fresh solution. The amount of fluoride released was measured with a combination of a fluoride ion selective electrode (Orion, Cambridge, Mass.) and the reference part of a combination pH electrode after combining equal volumes of test solution with total ionic strength adjustment buffer solution (Fisher Scientific). Fluoride standard solutions ranging from $1\times10^{-6}$ M to $1\times10^{-4}$ M were measured to form a calibration curve, which was used to determine the fluoride concentration. The results (FIGS. 1–3) clearly demonstrate the differences in calcium and phosphate release from the different fillers. It also shows the continuous release of calcium and phosphate over extended time periods and the slow release of fluoride.

Figure 4:
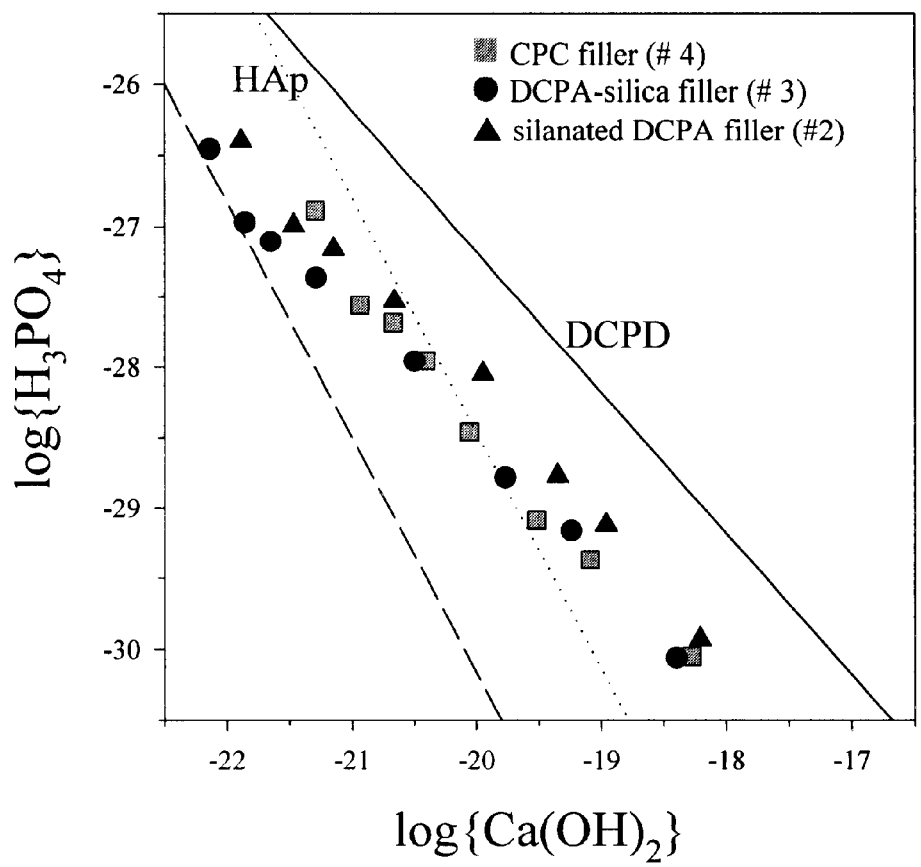
FIG. 4 is a "potential plot" of the log of phosphoric acid concentration versus the log of calcium hydroxide concentration demonstrating fluorapatite formation and hydroxyapatite formation for various calcium phosphate fillers.

From these data, a "potential plot" (FIG. 4) was generated according to the methods by Chow and Brown, 1984 and Vogel et al.,1990. In short, data points, which lie above a line characterizing a particular mineral, for example hydroxyapatite or fluorapatite, indicate that the solution is supersaturated with respect to that mineral. As all the points, which were calculated from the ion release data over a period of 58 days lie above the fluorapatite line and in part above the hydroxyapatite line, it is apparent that fluorapatite and some hydroxyapatite can be formed. Towards the end of the measurements (upper part of the plot) due to the high amount of fluor, the precipitated mineral will be mostly fluorapatite. Some calcium fluoride may also be formed.

These data are confirmed when the delta G values were calculated from the release of calcium, phosphate and fluoride ions.

Delta G was calculated from $$-2.0303(RT/n)\log(IAP/K_{sp})$$

where IAP is the ion activity product for hydroxyapatite or fluorapatite, $K_{sp}$ is the corresponding thermodynamic solubility product, R is the ideal gas constant, T is the absolute temperature and n is the number of ions in the ion activity product. Results are summarized in Tables 5 and 6.

TABLE 5

Remineralization potential (hydroxyapatite formation) of calcium phosphate-containing dentin bonding agents expressed as $\Delta G°$ (kJ/mol).

| | day 1 | | day 58 | |
| --- | --- | --- | --- | --- |
| | mean | sd | mean | sd |
| CPC (#4) | −1.47 | 0.08 | 0.88 | 0.58 |
| DCPA/silica (#3) | −1.02 | 0.06 | 3.86 | 0.26 |
| silanated DCPA (#2) | −1.75 | 0.37 | 1.60 | 0.12 |

TABLE 6

Remineralization potential (fluorapatite formation) of calcium phosphate-containing dentin bonding agents expressed as $\Delta G°$ (kJ/mol).

| | day 1 | | day 58 | |
| --- | --- | --- | --- | --- |
| | mean | sd | mean | sd |
| CPC (#4) | −5.16 | 0.07 | −4.23 | 0.54 |
| DCPA/silica (#3) | −4.77 | 0.08 | −1.90 | 0.31 |
| silanated DCPA (#2) | −5.55 | 0.40 | −3.74 | 0.10 |

The delta G values express the driving force that governs the salt formation from solutions supersaturated with respect to hydroxy- or fluorapatite, with a more negative number indicating a higher driving force and higher salt formation and clearly demonstrate the high potential of the single solution bonding formulation of the present invention to remineralize mineral deficient dentin through the formation of fluorapatite.

REFERENCES

Brown W E, Gregory T M, Chow L C (1977). Effects of fluoride on enamel solubility and cariostasis. *Caries Res* 11(Suppl 1): 118–141.

Brännstrom M (1984). Communication between the oral cavity and the dental pulp associated with restorative treatment. *Oper Dent* 9:57–68.

Chow L C, Brown W E (1984). A physicochemical bench-scale caries model. *J Dent Res* 63:868–873.

Chow L C, Takagi S, Tung W, Jordan T H (1991). Digital image analysis assisted microradiography-measurement of mineral content of caries lesions in teeth. *J Res Natl Inst Stand Technol* 96:203–214.

Chow L C, Takagi S, Shih S (1992). Effect of a two-solution fluoride mouthrinse on remineralization of enamel lesions in vitro. *J Dent Res* 71:443–447.

Cox C F, Keall C L, Ostro E, Bergenholtz G (1987). Biocompatibility of surface-sealed dental materials against exposed pulps. *J Prosth Dent* 57:1–8.

Cox C F, Suzuki S (1994). Re-evaluating pulp protection: calcium hydroxide liners vs. cohesive hybridization. *J Am Dent Assoc* 125:823–831.

Cox C F, Subay R K, Suzuki S, Suzuki S H, Ostro E (1996). Biocompatibility of various dental materials: pulp healing with a surface seal., *Int J Periodontics Restorative Dent* 16:240–51.

Dickens-Venz S, Bowen R L, Eichmiller FC (1992). TEM investigation of the dentin-adhesive interface of in vivo and in vitro bonded human teeth. *J Dent Res* 72: Abst. No. 1201

Dickens-Venz S H, Takagi S, Chow L C, Bowen R L, Johnston A D, Dickens B (1994). Physical and chemical properties of resin-reinforced calcium phosphate cements. *Dent Mater* 10:100–106.

Dickens S H, Takagi S, Liao H (1996). In-vitro properties of novel resin-reinforced calcium phosphate cements. *J Dent Res* 75:72, Abst. No. 435.

Dickens S H, Flaim G M, Takagi S, Liao H (1998). Remineralization of dentin and enamel lesions with calcium phosphate cements. *J Dent Res* 77:202, Abst. No. 769.

Ehudin D Z, Thompson V P (1994). Tensile bond strength of dental adhesives bonded to simulated caries-exposed dentin. *J Prosthet Dent* 71(2): 165–73.

Flaim G M, Dickens S H, Galloucis, T L, Takagi S (1999). In vitro properties of Ca—PO₄ resin cements with remineralization potential. *J Dent Res* 78:160, Abst. No. 434.

Flaim G M, Dickens S H (2001). Remineralization of dentin lesions from bonded and non-bonded Ca—PO4 resin cements. *J Dent Res* 80: Special Issue (AADR Abstract), Abst. No. 1306

Gwinnett A J, Tay F (1998). Early and intermediate time response of the dental pulp to an acid etch technique in vivo. *Am J Dent* 11 Spec Issue: S35–44

Kimochi T, Yoshiyama M, Urayama A, Matsuo T (1999). Adhesion of a new commercial self-etching/self-priming bonding resin to human caries-infected dentin. *Dent Mater J* 18:437–43.

LeGeros R Z (1990). Chemical and crystallographic events in the caries process. *J Dent Res* 69(Spec Issue): 567–574.

Nakabayashi N, Ashizawa M, Nakamura M (1992). Identification of a resin-dentin hybrid layer in vital human dentin created in vivo: durable bonding to vital dentin. *Quintessence Int* 23:135–41.

Nakajima M, Sano H, Burrow M F, Tagami J, Yoshiyama M, Ebisu S, Ciucchi B, Russell C M, Pashley D H (1995). Tensile bond strength and SEM evaluation of caries-affected dentin using dentin adhesives. *J Dent Res* 74:1679–88.

Nakajima M, Ogata M, Okuda M, Tagami J, Sano H, Pashley D H (1999 a). Bonding to caries-affected dentin using self-etching primers. *Am J Dent* 12:309–14.

Nakajima M, Sano H, Zheng L, Tagami J, Pashley D H (1999 b). Effect of moist vs. dry bonding to normal vs. caries-affected dentin with Scotchbond Multi-Purpose Plus. *J Dent Res* 78:1298–1303.

Perdigao J, Swift E J Jr, Denehy G E, Wefel J S, Donly K J (1994). In vitro bond strengths and SEM evaluation of dentin bonding systems to different dentin substrates. *J Dent Res* 73:44–55.

Stanley H R, Going RE, Chauncey H H (1975). Human pulp response to acid pretreatment of dentin and to composite restoration. *JADA* 91:817–825.

Stanley H R (1990). Pulpal responses to ionomer cements—biological characteristics. *JADA* 120:25–29.

Stanley H R (1998). Criteria for standardizing and increasing credibility of direct pulp-capping studies. *Am J Dent* 11 Spec Issue:S17–34. Review.

Tam L E, Pilliar R M (1994). Fracture surface characterization of dentin-bonded interfacial fracture specimens. *J Dent Res* 73:607–619.

Titley K, Chernecky R, Maric B, Valiquette N, Smith D (1994). The morphology of the demineralized layer in primed dentin. *Am J Dent* Feb;7(1):22–6.

Venz S, Dickens B (1993). Modified surface-active monomers for adhesive bonding to dentin. *J Dent Res* 72:582–586.

Van Meerbeek B, Inokoshi S, Braem M, Lambrechts P, Vanherle G (1992). Morphological aspects of the resin-dentin interdiffusion zone with different dentin adhesive systems. *J Dent Res* 71:1530–1540.

Vogel G L, Carey C M, Chow L C, Tatevossian A (1990). Micro-analysis of plaque fluid from single-site fasted plaque. *J Dent Res* 69:1316–1323.

Vogel G L, Chow L C, Brown W E (1983). A microanalytical procedure for the determination of calcium, phosphate and fluoride in enamel biopsy samples. *Caries Res* 17:23–31.

Yoshiyama M, Sano H, Ebisu S, Tagami J, Ciucchi B, Carvalho R M, Johnson M H, Pashley D H (1996). Regional strengths of bonding agents to cervical sclerotic root dentin. *J Dent Res* 75:1404–13.

I claim:

1. A single solution bonding formulation for dental applications comprising:
   a1) a plurality of a self-polymerizable polyvinyl acidic monomer or a plurality of at least two different polymerizable polyvinyl acidic monomers,
   b1) a calcium phosphate filler,
   c1) at least one polymerization photoinitiator,
   d1) optionally, an accelerator,
   e1) optionally, a solvent, and
   f1) optionally, a fluoride additive.

2. The formulation of claim 1 wherein said polymerizable polyvinyl acidic monomer (a1) is a polyvinyl acidic methacrylate monomer (a2).

3. The formulation of claim 2 further comprising an additive methacrylate monomer (a3).

4. The formulation of claim 2 wherein said acidic polyvinyl acidic methacrylate monomer (a2) is selected from the group consisting of:

a4) pyromellitic dianhydride GDM adduct (PMGDM),
b4) pyromellitic dianhydride HEMA adduct (PMDM),
c4) biphenyl dianhydride GDM adduct (BP-GDM),
d4) biphenyl dianhydride HEMA adduct (BP-HEMA),
e4) benzophenone-3,3',4,4'-tetracarboxylic dianhydride GDM adduct (BPh-GDM),
f4) benzophenone-3,3',4,4'-tetracarboxylic dianhydride HEMA adduct (BPh-HEMA),
g4) bicyclo[2.2.2]oct-7-ene-2,3,5,6-tetracarboxylic dianhydride GDM adduct (BCOE-GDM),
h4) bicyclo[2.2.2]oct-7-ene-2,3,5,6-tetracarboxylic dianhydride HEMA adduct (BCOE-HEMA),
i4) 5-(2,5dioxotetrahydro-3-furanyl)-3-cyclohexene-1,2-dicarboxylic anhydride GDM adduct (B4400-GDM),
j4) 5-(2,5dioxotetrahydro-3-furanyl)-3-cyclohexene-1,2-dicarboxylic anhydride HEMA adduct (B4400-HEMA),
k4) phthalic anhydride GDM adduct (PhTh-GDM), and
l4) combinations thereof.

5. The formulation of claim 3 wherein said additive methacrylate monomer (a3) is selected from the group consisting of:
   a5) 2-hydroxyethylmethacrylate (HEMA),
   b5) glycerol dimethacrylate (GDM),
   c5) ethyl-α-hydroxy methacrylate (EHMA),
   d5) tetrahydrofurfuryl methacrylate (THFM),
   e5) hydroxypropyl methacrylate (HPMA),
   f5) urethane dimethacrylate (UDMA),
   g5) ethoxylated bisphenol A dimethacrylate (EBPADMA),
   h5) 2,2'-bis[p-(2'-hydroxy-3'-methacryloxypropoxy)phenylene]propane (Bis-GMA),
   i5) phthalic anhydride HEMA adduct (PhTh-GDM); and
   j5) combinations thereof.

6. The formulation of claim 2 wherein said polymerizable polyvinyl acidic monomer (a2) comprises pyromellitic glycerol dimethacrylate (PMGDM) and said additive methacrylate monomer (a3) comprises 2-hydroxyethyl methacrylate (HEMA).

7. The formulation of claim 1 wherein said calcium phosphate filler (b1) is selected from the group consisting of:
   a7) dicalcium phosphate anhydrous (DCPA),
   b7) silanated DCPA,
   c7) dicalcium phosphate dihydrate (DCPD),
   d7) silanated DCPD,
   e7) calcium phosphate cement (CPC),
   f7) silanated CPC,
   g7) amorphous calcium phosphate, and
   h7) combinations thereof.

8. The formulation of claim 7 wherein said calcium phosphate filler (b1) comprises said DCPA (a7).

9. The formulation of claim 7 wherein said calcium phosphate filler (b1) comprises said DCPD (c7).

10. The formulation of claim 7 wherein said calcium phosphate filler comprises said CPC (e7).

11. The formulation of claim 7 wherein said silanated DCPA (b7) comprises
   DCPA silanated with methacryloylpropoxy-trimethoxysilane,
   methacryloylpropoxy-triethoxysilane, vinyl-trimethoxysilane, or vinyl-triethoxysilane.

12. The formulation of claim 7 wherein said silanated DCPD (d7) comprises DCPD silanated with methacryloylpropoxy-trimethoxysilane, methacryloylpropoxy-triethoxysilane, vinyl-trimethoxysilane, or vinyl-triethoxysilane.

13. The formulation of claim 7 wherein said silanated CPC (f7) comprises CPC silanated with methacryloylpropoxy-trimethoxysilane, methacryloylpropoxy-triethoxysilane, vinyl-trimethoxysilane, or vinyl-triethoxysilane.

14. The formulation of claim 10 wherein said CPC (e7) comprises (i) said DCPA (a7) and a tetracalcium phosphate (TTCP), (ii) said DCPD (c7) and said TTCP, or both (i) and (ii).

15. The formulation of claim 14 wherein said DCPA (a7) and said TTCP or said DCPD (c7) and said TTCP, are each provided in an amount sufficient to form hydroxyapatite when mixed with water.

16. The formulation of claim 15 wherein said CPC (e7) comprises about 1–99% by weight of said DCPA (a7) and about 99–1% by weight of said TTCP based on a total weight of said CPC (e7).

17. The formulation of claim 15 wherein said CPC (e7) comprises about 10–90% by weight of said DCPA (a7) and about 90–10% by weight of said TTCP based on a total weight of said CPC (e7).

18. The formulation of claim 15 wherein said CPC (e7) comprises about 20–80% by weight of said DCPA (a7) and about 80–20% by weight of said TTCP based on a total weight of said CPC (e7).

19. The formulation of claim 15 wherein said CPC (e7) comprises about 20–50% by weight of said DCPA (a7) and about 80–50% by weight of said TTCP based on a total weight of said CPC (e7).

20. The formulation of claim 15 wherein said CPC (e7) comprises about 20–40% by weight of said DCPA (a7) and about 80–60% by weight of said TTCP based on a total weight of said CPC (e7).

21. The formulation of claim 15 wherein said CPC (e7) comprises about 27% by weight of said DCPA (a7) and about 73% by weight of said TTCP based on a total weight of said CPC (e7).

22. The formulation of claim 15 wherein said CPC (e7) comprises about 30–70% by weight of said DCPD (c7) and about 70–30% by weight of said TTCP based on a total weight of said CPC (e7).

23. The formulation of claim 15 wherein said CPC (e7) comprises about 32% by weight of said DCPD (c7) and about 68% by weight of said TTCP based on a total weight of said CPC (e7).

24. The formulation of claim 7 wherein said calcium phosphate filler (b1) further comprises an inert filler.

25. The formulation of claim 24 wherein said inert filler is selected from the group consisting of:
   a25) a microfine silica,
   b25) a nanofiller, and
   c25) combinations thereof.

26. The formulation of claim 25 wherein said calcium phosphate filler (b1) comprises said DCPA (a7) and said microfine silica (a25).

27. The formulation of claim 26 wherein said DCPA (a7) and said microfine silica (a25) are each provided in an amount from about 50% by weight based on a total of said calcium phosphate filler (b1).

28. The formulation of claim 25 wherein said calcium phosphate filler (b1) comprises said DCPD (c7) and said microfine silica (a25).

29. The formulation of claim 25 wherein said DCPD (c7) and said microfine silica (a25) are each provided in an amount from about 50% by weight based on a total of said calcium phosphate filler (b1).

30. The formulation of claim 25 wherein said calcium phosphate filler (b1) comprises said CPC (e7) and said microfine silica (a25).

31. The formulation of claim 30 wherein said CPC (e7) and said microfine silica (a25) are each provided in an amount from about 50% by weight based on a total of said calcium phosphate filler (b1).

32. The formulation of claim 1 wherein said at least one polymerization photoinitiator (c1) is selected from the group consisting of:
   a32) a visible light activated photoinitiator,
   b32) an ultraviolet light activated photoinitiator, and
   c32) combinations thereof.

33. The formulation of claim 32 wherein said visible light activated photoinitiator (a32) is selected from the group consisting of: camphorquinone, benzil, mono-acylphosphine oxide, bis-acylphosphine oxide, and combinations thereof.

34. The formulation of claim 32 wherein said visible light activated photoinitiator (a32) is activated by light having a wavelength from about 365 nm to about 600 nm.

35. The formulation of claim 34 wherein said visible light activated photoinitiator is activated by exposing to light at said wavelength for a time from about 3 seconds to about 2 minutes.

36. The formulation of claim 32 wherein said ultraviolet light activated photoinitiator (b32) is selected from the group consisting of: phosphine oxides, 2,2-dimethoxy-2-phenylacetophenone, and combinations thereof.

37. The formulation of claim 32 wherein said ultraviolet light activated photoinitiator (b32) is activated by light having a wavelength from about 350 nm to about 395 nm.

38. The formulation of claim 32 wherein said ultraviolet light activated photoinitiator (b32) is activated by light having a wavelength from about 350 nm to about 380 nm.

39. The formulation of claim 37 wherein said ultraviolet light activated photoinitiator is activated by exposing to light at said wavelength for a time from about 3 seconds to about 2 minutes.

40. The formulation of claim 38 wherein said ultraviolet light activated photoinitiator is activated by exposing to light at said wavelength for a time from about 3 seconds to about 2 minutes.

41. The formulation of claim 1 wherein said optional accelerator (d1) is a tertiary amine.

42. The formulation of claim 41 wherein said tertiary amine comprises $R_1R_2$-N-$R_3$-X wherein $R_1$ and $R_2$ may be the same or different and are independently selected from the group consisting of an alkyl or alkanol, wherein $R_3$ is selected from the group consisting of aromatic or aliphatic, and wherein X is an electron withdrawing group.

43. The formulation of claim 1 wherein said solvent (d1) is selected from the group consisting of:
   a43) acetone,
   b43) ethanol,
   c43) water,
   d43) tetrahydro-furan
   e43) acetone and ethanol,
   f43) ethanol and water,
   g43) acetone and water, and
   h43) a mixture thereof.

44. The formulation of claim 43 wherein said solvent (d1) comprises about 25% by weight of said acetone (a43) and about 75% by weight of said ethanol (b43) based on a total weight of said solvent (d1).

45. The formulation of claim 43 wherein said solvent (d1) comprises about 50% by weight of said acetone (a43) and about 50% by weight of said ethanol (b43) based on a total weight of said solvent (d1).

46. The formulation of claim 43 wherein said solvent (d1) comprises about 75% by weight of said acetone (a43) and about 25% by weight of said ethanol (b43) based on a total weight of said solvent (d1).

47. The formulation of claim 43 wherein said solvent (d1) comprises about 7% by weight of said water (c43) and about 93% by weight of said ethanol (b43) based on a total weight of said solvent (d1).

48. The formulation of claim 43 wherein said solvent (d1) comprises about 3% by weight of said water (c43) and about 97% by weight of said ethanol (b43) based on a total weight of said solvent (d1).

49. The formulation of claim 43 wherein said solvent (d1) comprises about 1% by weight of said water (c43) and about 99% by weight of said ethanol (b43) based on a total weight of said solvent (d1).

50. The formulation of claim 1 wherein said solvent (d1) consists essentially of acetone.

51. The formulation of claim 1 wherein said solvent (d1) consists essentially of ethanol.

52. The formulation of claim 1 wherein said solvent (d1) consists essentially of acetone and ethanol.

53. The formulation of claim 1 wherein said formulation has a pH from about 3 to about 7.

54. The formulation of claim 1 wherein said formulation is provided as a member selected from the group consisting of:
  a54) a paste,
  b54) a creme,
  c54) a gel,
  d54) a solution,
  e54) an emulsion,
  f54) a dispersion, and
  g54) a suspension.

55. The formulation of claim 1 wherein, upon polymerization, said formulation has a shear bond strength of at least about 28 MPa when bonded to enamel or dentin.

56. The formulation of claim 1 wherein, upon polymerization, said formulation has a shear bond strength from about 28 MPa to about 37 MPa when bonded to enamel or dentin.

57. The formulation of claim 1 wherein, after polymerization of said polyvinyl acidic monomer (a1), said polymerized formulation of claim 1 permits diffusion of calcium, phosphate, or fluoride from said polymerized formulation into enamel, dentin, or pulp sufficient to form hydroxyapatite or fluorapatite or combinations thereof.

58. The formulation of claim 1 wherein, after polymerization of said monomer (a1), said polymerized formulation of claim 1 permits diffusion of:
  a58) calcium,
  b58) phosphate,
  c58) fluoride,
  d58) calcium and phosphate,
  e58) calcium and fluoride, or
  f58) calcium and phosphate and fluoride from said polymerized formulation into said enamel, dentin, or pulp.

59. The formulation of claim 58 wherein said calcium diffuses at a calcium diffusion rate from about 10 $\mu molL^{-1} day^{-1}$ to about 30 $\mu molL^{-1} day^{-1}$.

60. The formulation of claim 58 wherein said phosphate diffuses at a phosphate diffusion rate from about 65 $\mu molL^{-1} day^{-1}$ to about 135 $\mu molL^{-1} day^{-1}$.

61. The formulation of claim 58 wherein said fluoride diffuses at a fluoride diffusion rate from about 10 $\mu molL^{-1} day^{-1}$ to about 45 $\mu molL^{-1} day^{-1}$.

62. The formulation of claim 1 wherein said polymerizable monomer (a1) is provided in an amount from about 2.0% by weight to about 95% by weight based on a total weight of said single solution bonding formulation.

63. The formulation of claim 1 wherein said calcium phosphate filler (b1) is provided in an amount from about 2.5% by weight to about 50% by weight based on a total weight of said single solution bonding formulation.

64. The formulation of claim 1 wherein said at least one polymerization photoinitiator (c1) is provided in an amount from about 0.2% by weight to about 1.5% by weight based on a total weight of said single solution bonding formulation.

65. The formulation of claim 1 wherein said optional solvent (d1) is provided in an amount from about 0% by weight to about 80% by weight based on a total weight of said single solution bonding formulation.

66. The formulation of claim 62 wherein said calcium phosphate filler (b1) is provided in an amount from about 2.5% by weight to about 40% by weight based on a total weight of said single solution bonding formulation.

67. The formulation of claim 66 wherein said at least one polymerization photoinitiator (c1) is provided in an amount from about 0.4% by weight to about 1.6% by weight based on a total weight of said single solution bonding formulation.

68. The formulation of claim 67 wherein said accelerator (d1) is provided in an amount from about 0% by weight to about 0.6% by weight based on a total weight of said single solution bonding formulation.

69. The formulation of claim 68 wherein said solvent (e1) is provided in an amount from about 0% by weight to about 80% by weight based on a total weight of said single solution bonding formulation.

70. The formulation of claim 1 further comprising said fluoride additive.

71. The formulation of claim 70 wherein said fluoride additive is selected from the group consisting of: sodium hexafluorosilicate, sodium hexafluorophosphate, sodium hexafluoroantimonate, sodium fluoride, sodium monofluor phosphate, potassium hexafluorosilicate, potassium hexafluorophosphate, potassium hexafluoroantimonate, and combinations thereof.

72. A method of preparing a single solution bonding formulation of claim 1, said method comprising the step of:
  a72) mixing together:
    aa72) a plurality of a self-polymerizable polyvinyl acidic monomer or a plurality of at least two different polymerizable polyvinyl acidic monomers,
    bb72) a calcium phosphate filler,
    cc72) at least one polymerization photoinitiator,
    dd72) optionally, an accelerator,
    ee72) optionally, a solvent, and
    ff72) optionally, a fluoride additive.

73. A method for treating enamel, dentin, or exposed pulp in need thereof, comprising the step(s) of:
  a73) applying to said enamel, dentin, enamel, or exposed pulp said single solution bonding formulation of claim 1, b73) then exposing said single solution bonding formulation to light sufficient to polymerize said single solution bonding formulation of claim 1.

74. The method of claim 73 wherein said light has a wavelength from about 350 nm to about 600 nm.

75. The method of claim 73 wherein said exposing step (b72) comprises exposing said formulation to light for an exposure time sufficient to polymerize said single solution bonding formulation.

76. The method of claim 75 wherein said exposure time is from about 3 seconds to about 2 minutes.

77. The method of claim 73 further comprising a conditioning step comprising conditioning said dentin or enamel before said applying step (a72).

78. The method of claim 77 wherein said conditioning step further comprises a78) exposing said dentin or enamel to a conditioning solution, and b78) then washing away said conditioning solution.

79. The method of claim 73 wherein said enamel, dentin, or pulp belong to a mammal.

80. The method of claim 79 wherein said mammal is a human.

81. The formulation of claim 1 wherein said polyvinyl acidic monomer is provided in an amount from about 20% to about 80% by weight based on a total weight of said single solution bonding formulation.

82. The formulation of claim 81 wherein said polyvinyl acidic monomer is provided in an amount from about 30% to about 80% by weight based on a total weight of said single solution bonding formulation.

83. The formulation of claim 82 wherein said polyvinyl acidic monomer is provided in an amount from about 30% to about 60% by weight based on a total weight of said single solution bonding formulation.

84. The formulation of claim 83 wherein said polyvinyl acidic monomer is provided in an amount from about 30% to about 45% by weight based on a total weight of said single solution bonding formulation.

85. The formulation of claim 5 wherein said additive methacrylate monomer is provided in an amount from about 1% to about 50% by weight based on a total weight of said single solution bonding formulation.

86. The formulation of claim 85 wherein said additive methacrylate monomer is provided in an amount from about 5% to about 40% by weight based on a total weight of said single solution bonding formulation.

87. The formulation of claim 86 wherein said additive methacrylate monomer is provided in an amount from about 5% to about 30% by weight based on a total weight of said single solution bonding formulation.

88. The formulation of claim 87 wherein said additive methacrylate monomer is provided in an amount from about 7% to about 25% by weight based on a total weight of said single solution bonding formulation.

89. The formulation of claim 88 wherein said additive methacrylate monomer is provided in an amount from about 9% to about 20% by weight based on a total weight of said single solution bonding formulation.

90. The formulation of claim 89 wherein said additive methacrylate monomer is provided in an amount from about 10% to about 15% by weight based on a total weight of said single solution bonding formulation.

* * * * *